US010441451B2

(12) United States Patent
Ostergard (10) Patent No.: US 10,441,451 B2
(45) Date of Patent: Oct. 15, 2019

(54) ANKLE BRACE

(71) Applicant: Doak Ostergard, Lincoln, NE (US)

(72) Inventor: Doak Ostergard, Lincoln, NE (US)

(73) Assignee: JOCDOC, LLC, Lincoln, NE (US)

( * ) Notice: Subject to any disclaimer, the term of this patent is extended or adjusted under 35 U.S.C. 154(b) by 1482 days.

(21) Appl. No.: 14/340,992

(22) Filed: Jul. 25, 2014

(65) Prior Publication Data
US 2015/0313743 A1 Nov. 5, 2015

Related U.S. Application Data

(63) Continuation-in-part of application No. 13/871,094, filed on Apr. 26, 2013, now abandoned, which is a continuation-in-part of application No. 13/134,087, filed on May 27, 2011, now Pat. No. 8,657,773.

(51) Int. Cl.
*A61F 5/00* (2006.01)
*A61F 5/01* (2006.01)

(52) U.S. Cl.
CPC .................. *A61F 5/0111* (2013.01)

(58) Field of Classification Search
CPC .... A61F 5/0111; A61F 5/0113; A61F 5/0104; A61F 5/01; A61F 13/066; A61F 13/065; A61F 13/067; A61F 13/06; A61F 5/00; A43B 5/00; A43B 7/20; A43B 7/18; A43B 7/14; A43B 5/18; A43C 11/004; A43C 11/006; A43C 19/00
USPC ........................ 602/27; 36/132, 136, 138, 69
See application file for complete search history.

(56) References Cited

U.S. PATENT DOCUMENTS

| | | |
|---|---|---|
| 4,621,648 A | 11/1986 | Ivany |
| 5,016,623 A | 5/1991 | Krahenbuhl |
| 6,775,929 B2 | 8/2004 | Katz et al. |
| 8,657,773 B2 | 2/2014 | Ostergard |
| 2008/0082034 A1 | 4/2008 | Wilkerson |
| 2008/0306422 A1 | 12/2008 | McChesney et al. |
| 2009/0216167 A1 | 8/2009 | Harris |
| 2009/0247923 A1 | 10/2009 | Lundberg |
| 2012/0302933 A1 | 11/2012 | Ostergard |

*Primary Examiner* — Victoria J Hicks
(74) *Attorney, Agent, or Firm* — Dennis L. Thomte; Thomte Patent Law Office LLC (57) ABSTRACT

An ankle brace which is positioned on an ankle of a person which incorporates a tensioning structure which permits full range of motion to the ankle joint but which prevents the ankle joint from moving past its normal range of motion to protect the ankle joint. An optional ankle strap system is also provided.

3 Claims, 6 Drawing Sheets

ANKLE BRACE

CROSS REFERENCE TO RELATED APPLICATION

This is a Continuation-In-Part application of application Ser. No. 13/871,094 filed Apr. 26, 2013 entitled ANKLE BRACE, which is a Continuation-In-Part application of Ser. No. 13/134,087, filed May 27, 2011 entitled ANKLE BRACE, now U.S. Pat. No. 8,657,773, issued Feb. 25, 2014.

BACKGROUND OF THE INVENTION

Field of the Invention

This invention relates to an ankle brace and more particularly to an ankle brace including a tensioning system which functionally stabilizes the ankle as it reaches extreme ranges of motion. Even more particularly, this invention relates to an optional ankle strap system which may be used to further stabilize the ankle.

Description of the Related Art

Conventional braces for protecting joints of the body do so by restricting or limiting motion of the joint to which it is applied to prevent a new injury or to protect a pre-existing injury. An ankle joint, just like all the joints in the human body, has a natural range of motion that it can move through without causing damage to itself. As it reaches the end of these ranges, the body has structure such as ligaments and tendons to create tension to end range of motion and protect the joint. Many of the prior art ankle braces do prevent the ankle from exceeding its extreme ranges of motion but do not provide the necessary flexibility to permit the athlete to function normally.

Applicant's ankle brace described and shown in the co-pending application and the issued patent, represent improvements in the ankle brace art. The instant invention represents a further improvement in the ankle brace art.

SUMMARY OF THE INVENTION

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

An ankle brace is disclosed for use with a cleated athletic shoe having a sole with a lower surface, with cleats extending downwardly therefrom, a lateral side, a medial side, an upper part with an upper end, a lacing closure with upper and lower ends, including a plurality of spaced-apart pairs of eyelets adapted to have a shoe lace threaded therein. The brace of this invention includes a flexible lateral portion having an upper end, a lower end, a forward end, a rearward end, an outer side and an inner side. The upper end of the lateral portion preferably has first, second and third spaced-apart eyelets formed therein at the forward end thereof. The lateral portion also has fourth and fifth eyelets formed therein rearwardly of the third eyelet thereof. An upwardly extending first loop is secured to the outer side of the lateral portion adjacent the eyelets at the forward end thereof. An upwardly extending second loop is secured to the outer side of the lateral portion rearwardly of the first loop. The lateral portion is removably positioned adjacent the lateral side of the upper part of the shoe.

The ankle brace also includes a flexible medial portion having an upper end, a lower end, a forward end, a rearward end, an outer side and an inner side. The upper end of the medial portion preferably has first, second and third spaced-apart eyelets formed therein at the forward end thereof. The medial portion also has fourth and fifth eyelets formed therein rearwardly of the third eyelet thereof. An upwardly extending first loop is secured to the outer side of the medial portion rearwardly of the fourth and fifth eyelets thereof. An upwardly extending second loop is secured to the outer side of the medial portion rearwardly of the first loop. A patch or strip of hook fasteners is secured to the outer surface of the medial portion at the rearward end thereof.

Preferably, the lateral and medial portions are of one-piece construction with the lower ends of the lateral and medial portions being connected by a bottom portion which extends between the lower ends of the lateral and medial portions beneath the sole of the shoe. The rearward ends of the lateral and medial portions are spaced apart.

The ankle brace of this invention also includes a flexible and stretchable body member having upper and lower ends, a lateral side portion, a medial side portion, and a heel portion. The lower end of the lateral side portion of the body member is secured to the lateral portion. The lower end of the medial side portion of the body member is secured to the medial portion. The heel portion of the body member is secured to the spaced-apart rearward ends of the lateral and medial portions and extends therebetween.

A flexible and stretchable first strap is provided having a first end, a second end, an upper end, a lower end, and inner and outer sides. The lower end of the first strap is secured to the upper end of the body member so that the first and second ends of the first strap extend forwardly from the body member. The outer side of the first strap has loop fasteners thereon. The brace also includes a second flexible strap having a first end, a second end, an outer side and an inner side. The first end of the second strap is secured to the first end of the first strap. The inner side of the second strap has hook fasteners thereon for adjustable attachment to the loop fasteners on the first strap at the second end of the first strap. A flexible, non-stretchable third strap is provided having first and second ends with the third strap being secured to the outer side of the first strap. The first end of the third strap has a pair of eyelets formed therein. The second end of the third strap has a pair of eyelets formed therein. A lace adjustably connects the eyelets on the third strap. A strip of loop fasteners is secured to the outer side of the third strap.

A downwardly extending first loop is secured to the third strap at the first end thereof. A downwardly extending second loop is secured to the third strap rearwardly of the first loop thereof. A downwardly extending third loop is secured to the third strap at the second end thereof. A downwardly extending fourth loop is secured to the third strap at the second end thereof rearwardly of the third loop. A flexible lateral anchor strap is secured to the third strap rearwardly of the second loop thereon and is secured to the lateral portion rearwardly of the second loop thereon so as to extend therebetween. A flexible medial anchor strap is secured to the third strap rearwardly of the fourth loop thereof and is secured to the medial portion rearwardly of the second loop thereof so as to extend therebetween.

The ankle brace of this invention includes a flexible and stretchable lateral tensioning cord having first and second ends. The first end of the lateral tensioning cord is fixed to the inner side of the lateral portion and extends outwardly through the fourth eyelet of the lateral portion. The lateral tensioning cord extends from its fixed first end upwardly and rearwardly through the first loop on the third strap, thence downwardly and rearwardly through the second loop on the lateral portion, thence around the lateral anchor strap, thence through the second loop on the third strap, thence downwardly and forwardly through the first loop on the lateral portion. The second end of the lateral tensioning cord extends through the fifth eyelet of the lateral portion and is secured to the lateral portion.

A flexible and stretchable medial tensioning cord is also provided having first and second ends with the first end of the medial tensioning cord being fixed to the inner side of the medial portion. The medial tensioning cord extends outwardly through the fourth eyelet of the medial portion. The medial tensioning cord then extends upwardly and rearwardly through the third loop on the third strap, thence downwardly and rearwardly through the second loop on the medial portion, thence around the medial anchor strap, thence forwardly through the fourth loop on the third strap, thence downwardly and forwardly through the first loop on the medial portion, thence downwardly through the fifth eyelet of the medial portion and is secured to the inner side of the medial portion.

The ankle brace also includes fourth and fifth straps having first and second ends. The first end of the fourth strap is secured to the lateral tensioning cord. The second end of the fourth strap is adjustably secured to the second end of the third strap. The fifth strap has its first end secured to the medial tensioning cord and has its second end selectively adjustably secured to the first end of the third strap. The ankle brace of this invention permits the wearers ankle to move through its normal range of motion and yieldably prevents the ankle from moving beyond its normal range motion thereby protecting the ankle.

The ankle brace also includes an optional one-piece ankle strap. The ankle strap is selectively secured, intermediate its length, to the heel portion to define first and second ankle strap members. The first ankle strap member extends forwardly from the heel portion adjacent the lateral portion, thence downwardly therefrom, thence beneath the lower ends of the lateral and medial portions, thence upwardly and rearwardly towards the first end of the third strap, with the second end of the first ankle strap member being adjustably secured to the third strap at the first end thereof.

The second ankle strap member extends forwardly from the heel portion adjacent the medial portion, thence downwardly therefrom, thence beneath the lower ends of the medial and lateral portions, thence upwardly and rearwardly towards the second end of the third strap, with the second end of the second strap being adjustably secured to the third strap at the second end thereof.

The ankle strap system is designed to provide additional support to the ankle should it be necessary or desired.

It is therefore a principal object of the invention to provide an improved ankle brace.

A further object of the invention is to provide an ankle brace for use with a cleated athletic shoe which permits the wearer's ankle to move through its normal range of motion but which yieldably prevents the ankle from moving beyond its normal range of motion thereby protecting the ankle.

A further object of the invention is to provide an ankle brace of the type described which does not interfere with the normal movement of the person's ankle.

A further object of the invention is to provide an optional ankle strap system.

These and other objects will be apparent to those skilled in the art.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DESCRIPTION OF THE PREFERRED EMBODIMENT

Embodiments are described more fully below with reference to the accompanying figures, which form a part hereof and show, by way of illustration, specific exemplary embodiments. These embodiments are disclosed in sufficient detail to enable those skilled in the art to practice the invention. However, embodiments may be implemented in many different forms and should not be construed as being limited to the embodiments set forth herein. The following detailed description is, therefore, not to be taken in a limiting sense in that the scope of the present invention is defined only by the appended claims.

The disclosure of the co-pending application Ser. No. 13/871,094 filed Apr. 26, 2013 entitled ANKLE BRACE is incorporated herein by reference thereto to complete this disclosure if necessary.

The ankle brace of this invention is referred to generally by the reference numeral 10. Ankle brace 10 is designed to be attached to an athletic shoe 12 having a sole 14 and an upper part 16. A plurality of cleats 18 extend downwardly from the underside of sole 14. Upper part 16 has a lacing closure structure 20 having a lower end 22 and an upper end 24. Lacing closure 20 has a plurality of eyelets, grommets or lace openings 26 designed to receive a shoelace 28 in conventional fashion. Shoe 14 will be described as having a lateral side 30, a medial side 32 and a heel counter 34.

Ankle brace 10 includes a lateral portion 36 having a forward end 38, a rearward end 40, an upper end 42 and a lower end 44. Lateral portion 36 is comprised of a flexible, non-stretchable material such as polyester. The inner side of lateral portion 36 has a flexible, non-stretchable reinforcing or stiffening member (not shown) secured to the upper portion thereof by stitching or the like. The upper forward end of lateral portion 36 has a plurality of spaced-apart grommets or eyelets 48 formed therein. Preferably, three eyelets 48 are formed in lateral portion 36. Grommets 50 and 51 are formed in lateral portion 36 rearwardly of the rearward-most grommet 48. Upwardly extending loops 52 and 54 are secured to the outer surface of lateral portion 36 rearwardly of the eyelets 50 and 51.

Ankle brace 10 also includes a medial portion 56 having a forward end 58, a rearward end 60, an upper end 62 and a lower end 64. Medial portion 56 is comprised of a flexible, non-stretchable material such as polyester. The lower end 64 of medial portion 56 and the lower end 44 of lateral portion 36 have a bottom member 66 which extends therebetween beneath the sole 14. Member 66 could be of two-piece construction if so desired. Bottom member 66 has openings 68 and 70 formed therein. The upper forward end of medial portion 56 has a plurality of spaced-apart grommets or eyelets 74 formed therein, the number of which is equal to the number of grommets or eyelets 48 formed in lateral portion 36. Grommets 76 and 78 are formed in medial portion 56 rearwardly of the rearward-most grommet 74.

Figure 6:
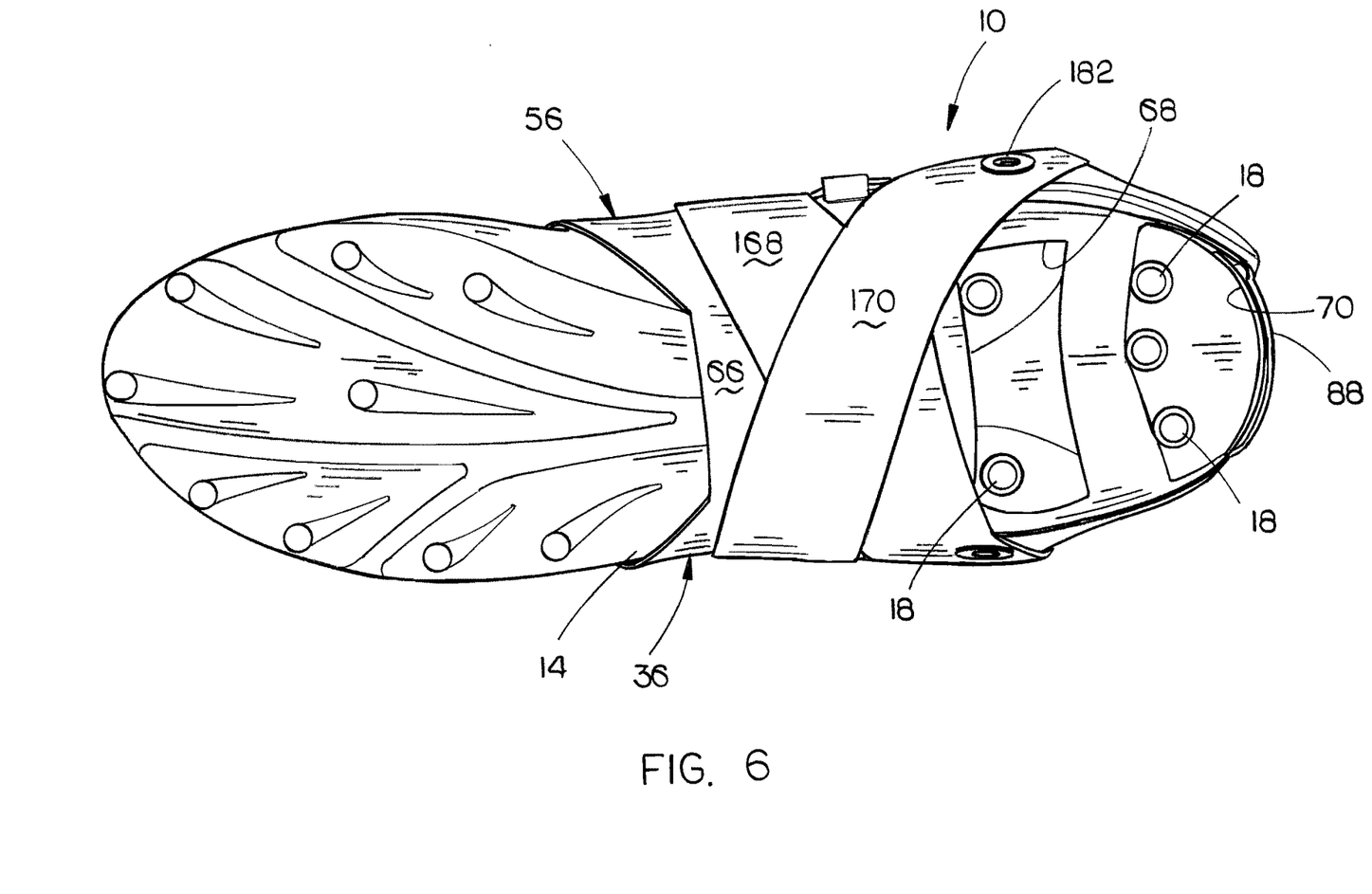
FIG. 6 is a bottom view of the ankle brace of this invention mounted on a shoe.

An upwardly extending loop 80 is secured to the outer surface of medial portion 56 rearwardly of the rearward most grommet 74. An upstanding loop 82 is secured to the outer surface of medial portion 56 below grommet 78. The upper rearward end of medial portion 56 has a strip 84 of hook fasteners secured thereto at the outer surface thereto. As seen in FIG. 6, the rearward ends of lateral portion 36 and medial portion 56 are spaced-apart. The upper rearward end of lateral portion 36 has a first strap 88 secured thereto which extends horizontally therefrom. The inner surface of strap 88 has loop fasteners 90 thereon to enable the strap 88 to be adjustably secured to the strip 84.

The numeral 92 refers to a flexible and stretchable body member preferably comprised of neoprene or the like which is secured to lateral portion 36 and medial portion 62 as will now be described. Body member 92 includes a lateral side portion 94, a medial side portion 96 and a heel portion 98. The lower end of lateral side portion 94 of body member 92 is secured to the upper end of lateral portion 36 by stitching or the like. The lower end of medial side portion 96 is secured to the upper end of medial portion 56 by stitching or the like. Heel portion 98 is positioned between the rearward ends of lateral portion 36 and medial portion 56 and is secured thereto by stitching or the like.

The numeral 100 refers to an elongated second strap having ends 102 and 104, an upper end 106 and a lower end 108. The lower end 108 of strap 100 is secured to the upper end of flexible and stretchable body member 92 so that the ends 102 and 104 extend forwardly from the forward ends of flexible and stretchable body member 92. The outer surface of strap 100 has loop fastener material thereon.

A short third strap 110 has one end secured to end 102 of strap 100 and extends therefrom. The inner side of strap 110 has hook fasteners 111 thereon for adjustable connection to the loop fasteners on the outer side of end 104 of strap 100.

A flexible and non-stretchable fourth strap 112, having ends 114 and 116, is secured to strap 100 at the outer side thereof by stitching or the like. Grommets 118 and 120 are formed in the end 114 of strap 112. Grommets 122 and 124 are formed in the end 116 of strap 112. A lace adjustably connects grommets 118, 120, 122 and 124 as in the co-pending application. An elongated strip 126 of loop fasteners is secured to the outer surface of strap 112. Downwardly extending loops 128 and 130 are secured to strap 112 adjacent end 114 thereof. Downwardly extending loops 132 and 134 are secured to strap 112 adjacent end 114 of strap 112. A flexible anchor strap 136 is secured to strap 112 and medial portion 56 and extends therebetween rearwardly of loops 130 and 82. The anchor strap 136 could have both if its ends secured to medial portion 56 so as to form an anchor loop. A flexible anchor strap 138 is secured to strap 112 and lateral portion 36 and extends therebetween rearwardly of loops 134 and 54. The anchor strap 138 could have both of its ends secured to lateral portion 36 so as to form an anchor loop.

The numeral 140 refers to a lateral tensioning cord which interconnects lateral portion 36 and strap 112. One end of cord 140 is secured to the inner side of lateral portion 36 at 142 and extends outwardly through grommet 50. Cord 140 extends through loop 132, thence through loop 54, thence around or through anchor strap 138, thence through loop 134, thence through loop 52, and thence through grommet 52. The other end of cord 140 is secured to lateral portion 36 at 144. In the alternative, the ends of cord 140 could be joined together rather than being secured to lateral portion 36.

The numeral 146 refers to a medial tensioning cord which interconnects medial portion 56 and strap 112. One end of cord 146 is secured to the inner side of medial portion 56 and extends outwardly through grommet 76. Cord 146 then extends through loop 128, thence through loop 82, thence around anchor strap 136, thence through loop 130, thence through loop 80, and thence through grommet 78. The other end of cord 146 is secured to the inner side of medial portion 56. In the alternative, the ends of cord 146 could be joined together rather than being secured to medial portion 56.

The numeral 148 refers to an elongated flexible strap having one end thereof secured to lateral tensioning cord 140. The free end of strap 148 has hook fasteners 150 on the inside surface thereof and loop fasteners 152 on the outer surface thereof. The free end of strap 148 may be adjustably secured to the loop fasteners 126 on the outer surface of strap 112 at the medial side thereof.

The numeral 149 refers to a strip or patch which is secured to the outer side of medial portion 56. The outer surface of strip 149 has loop fasteners thereon. The free end of strap 148 may be adjustably secured to the outer surface of strip 149 rather than the loop fasteners 126 on the outer surface of strap 112.

The numeral 154 refers to an elongated flexible strap having one end thereof secured to medial tensioning cord 146. The free end of strap 154 has hook fasteners on the inside surface thereof and loop fasteners 156 on the outer surface thereof. The free end of strap 154 is adjustably secured to the loop fasteners 126 on the outer surface of strap 112 at the lateral side thereof. The numeral 157 refers to a strip or patch which is secured to the outer side of lateral portion 36. The outer surface of strip 157 has loop fasteners thereon. The free end of strap 154 may be adjustably secured to the outer surface of strip 157 rather than the loop fasteners 126 on the outer surface of strap 112.

Figure 1:
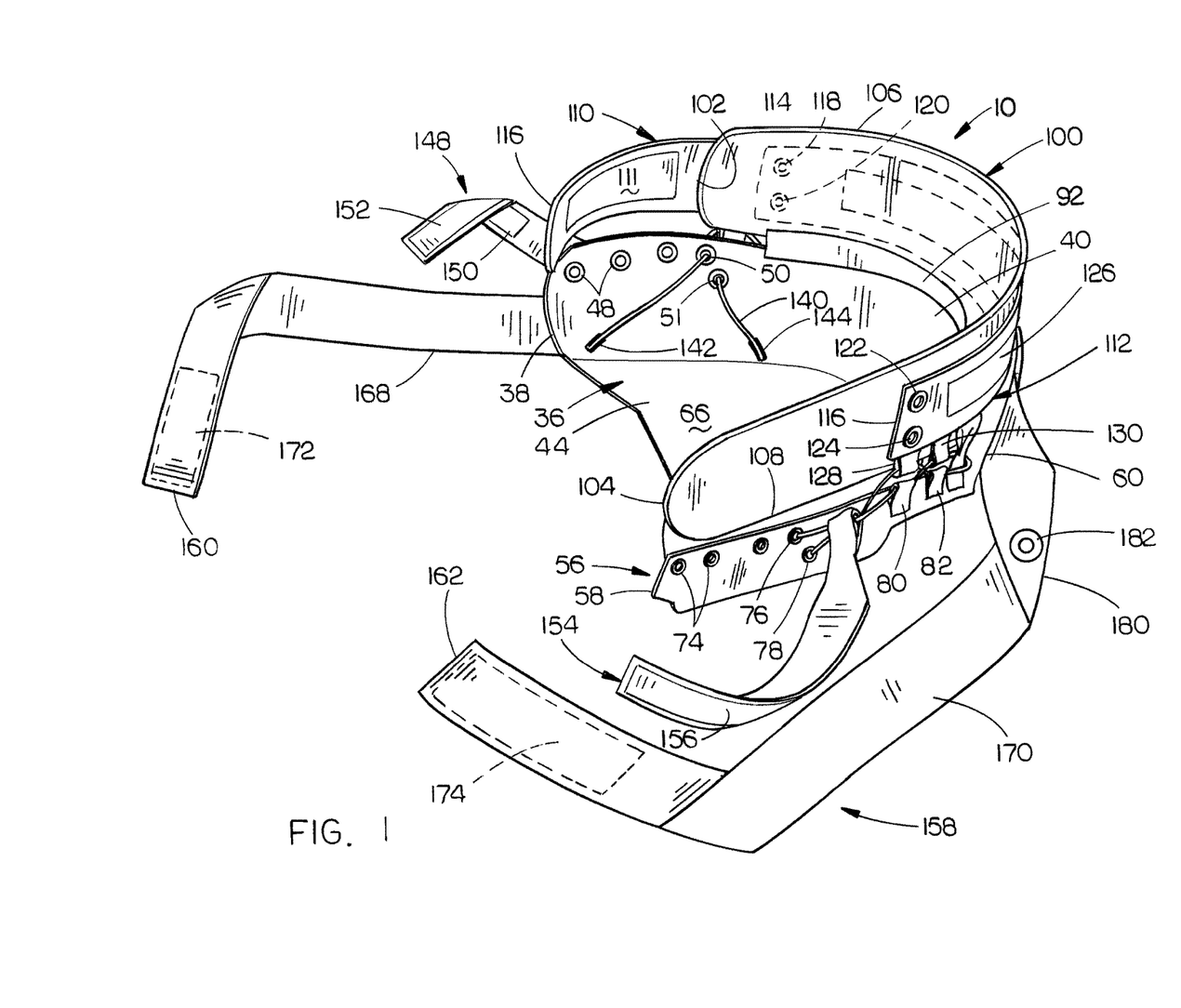
FIG. 1 is a perspective view of the ankle brace of this invention.
Figure 2:
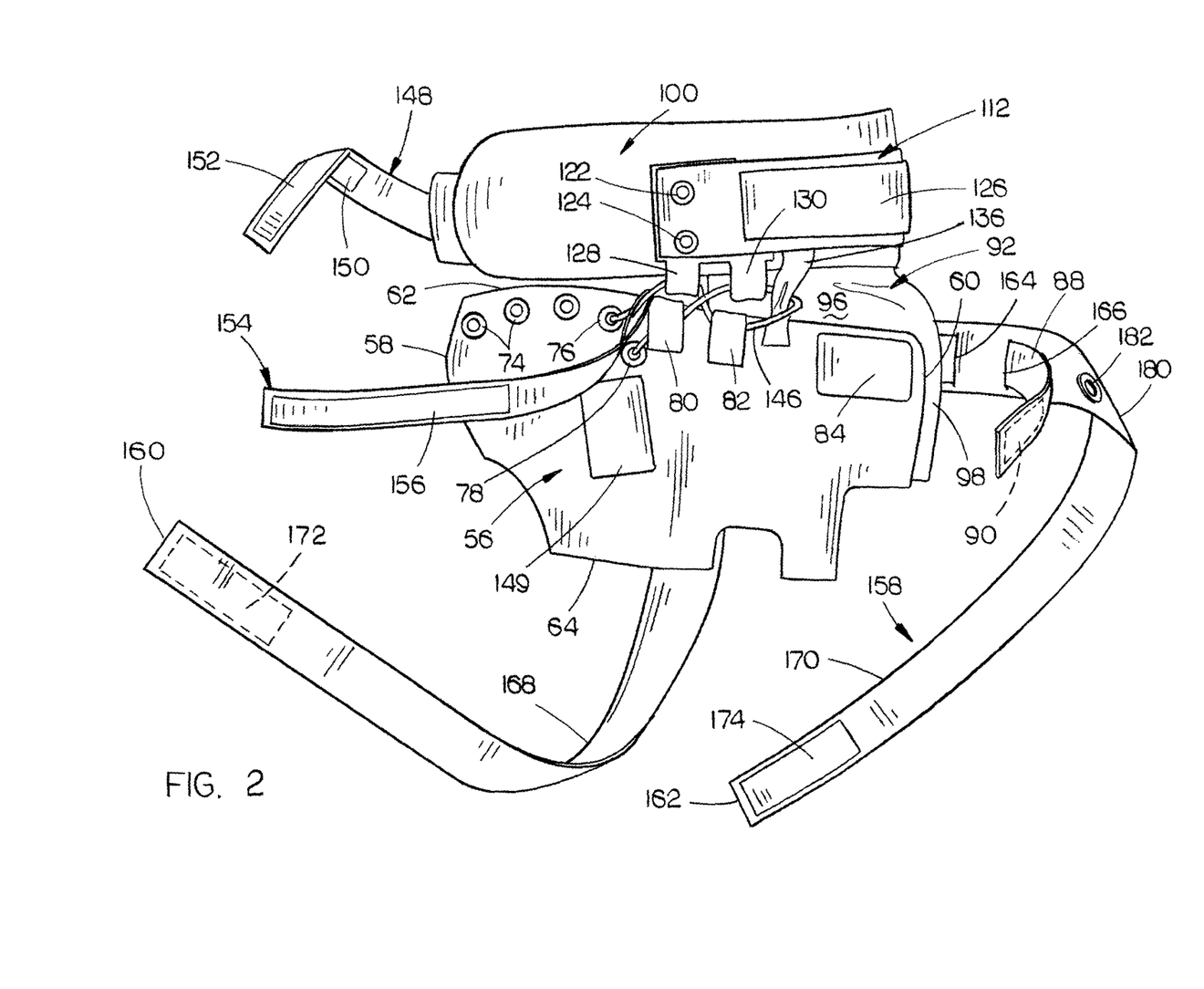
FIG. 2 is a medial side view of the invention.
Figure 3:
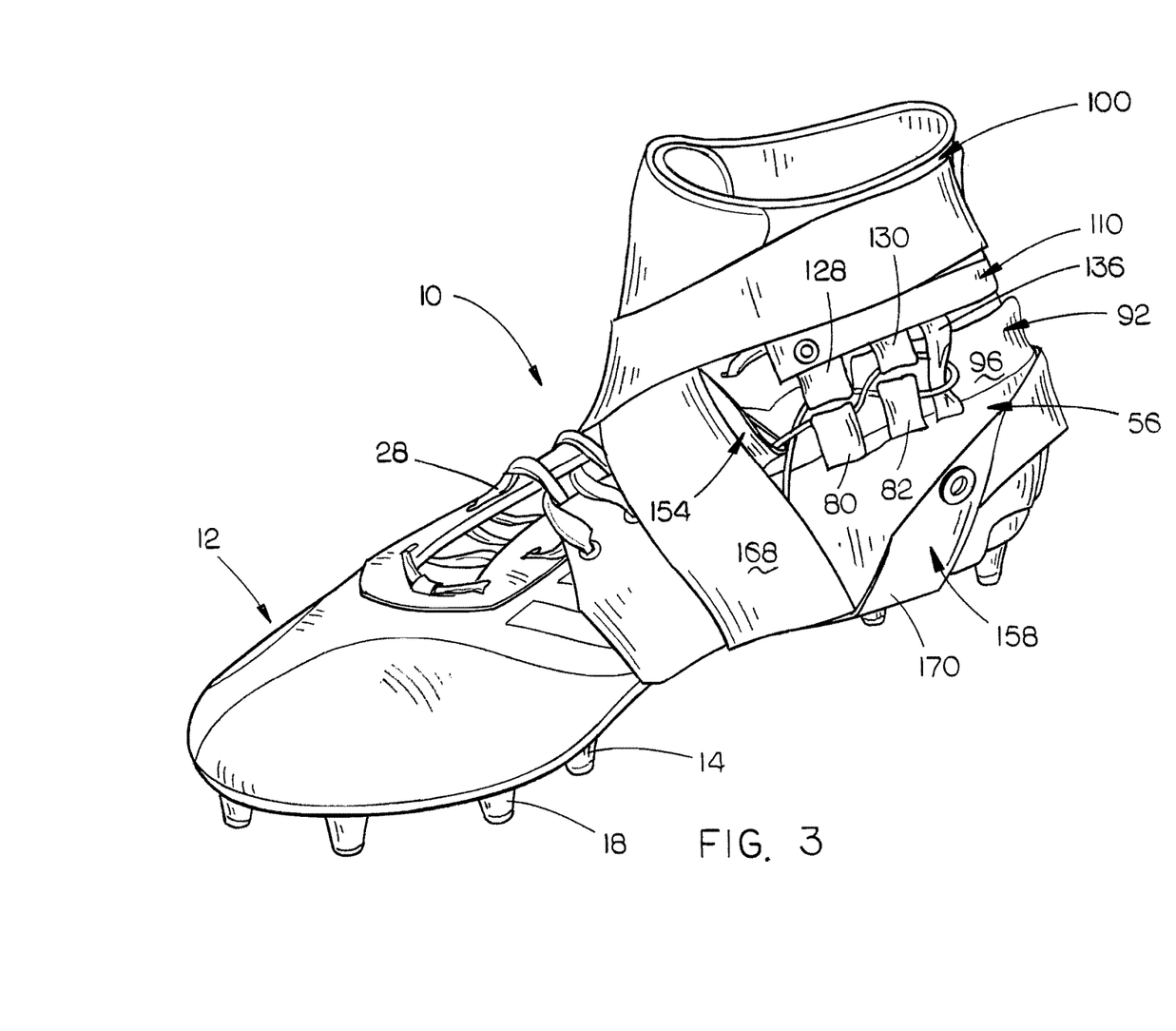
FIG. 3 is a perspective view illustrating the ankle brace of this invention mounted on a cleated shoe.
Figure 4:
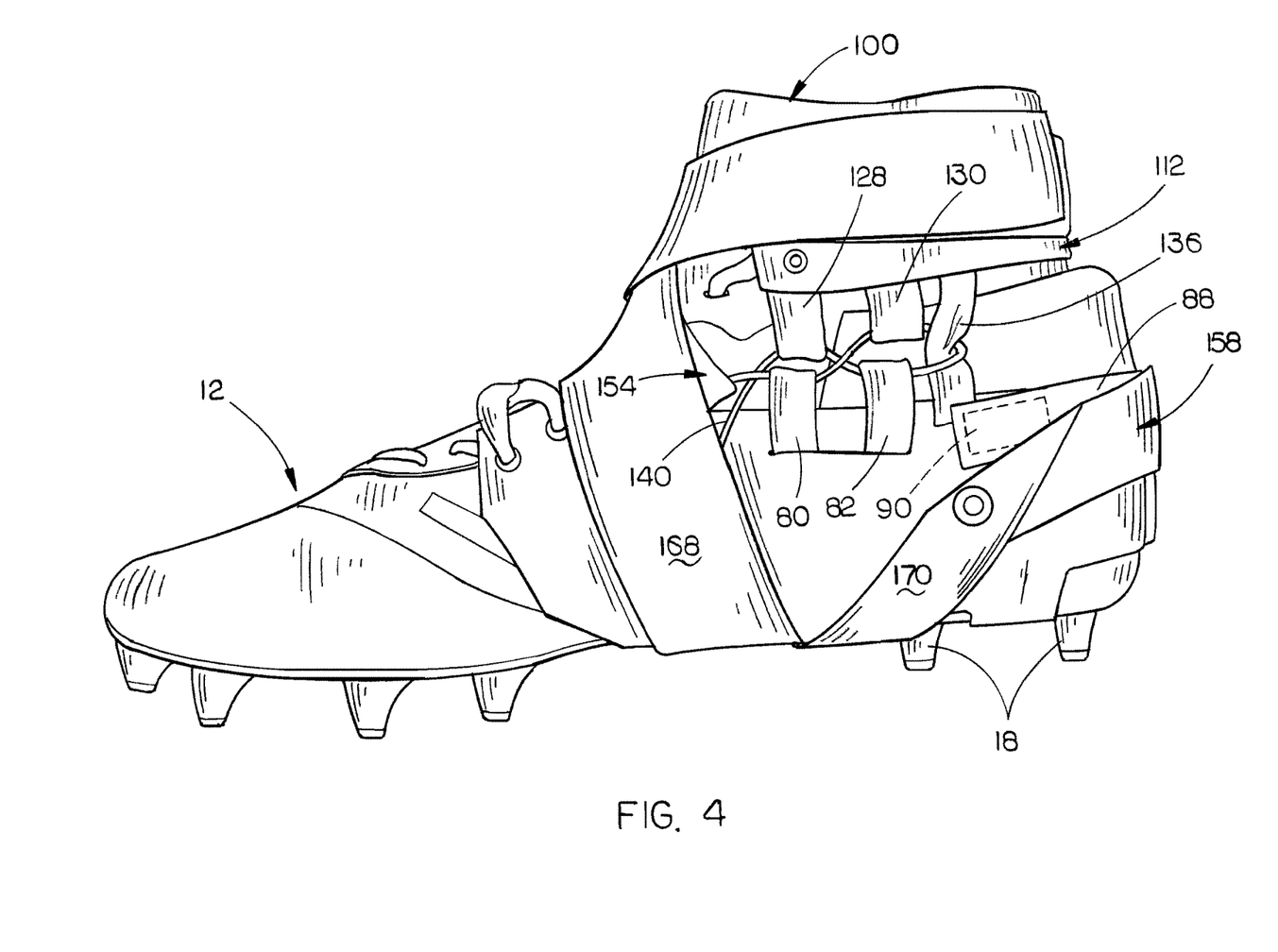
FIG. 4 is a medial side view of the ankle brace of this invention mounted on a shoe.

The numeral 158 refers to an optional ankle strap having ends 160 and 162. Ankle strap 158 has a pair of slits 164 and 166 formed therein intermediate the ends thereof. Strap 88 extends through slits 164 and 166 as seen in FIG. 2. The free end of strap 88 is then attached to the loop fasteners 84 on medial portion 56 to define ankle strap portions 168 and 170. The free end of ankle strap portion 168 has hook fasteners 172 at the inner side thereof. The free end of ankle strap portion 170 has hook fasteners 174 on the inner side thereof.

Figure 5:
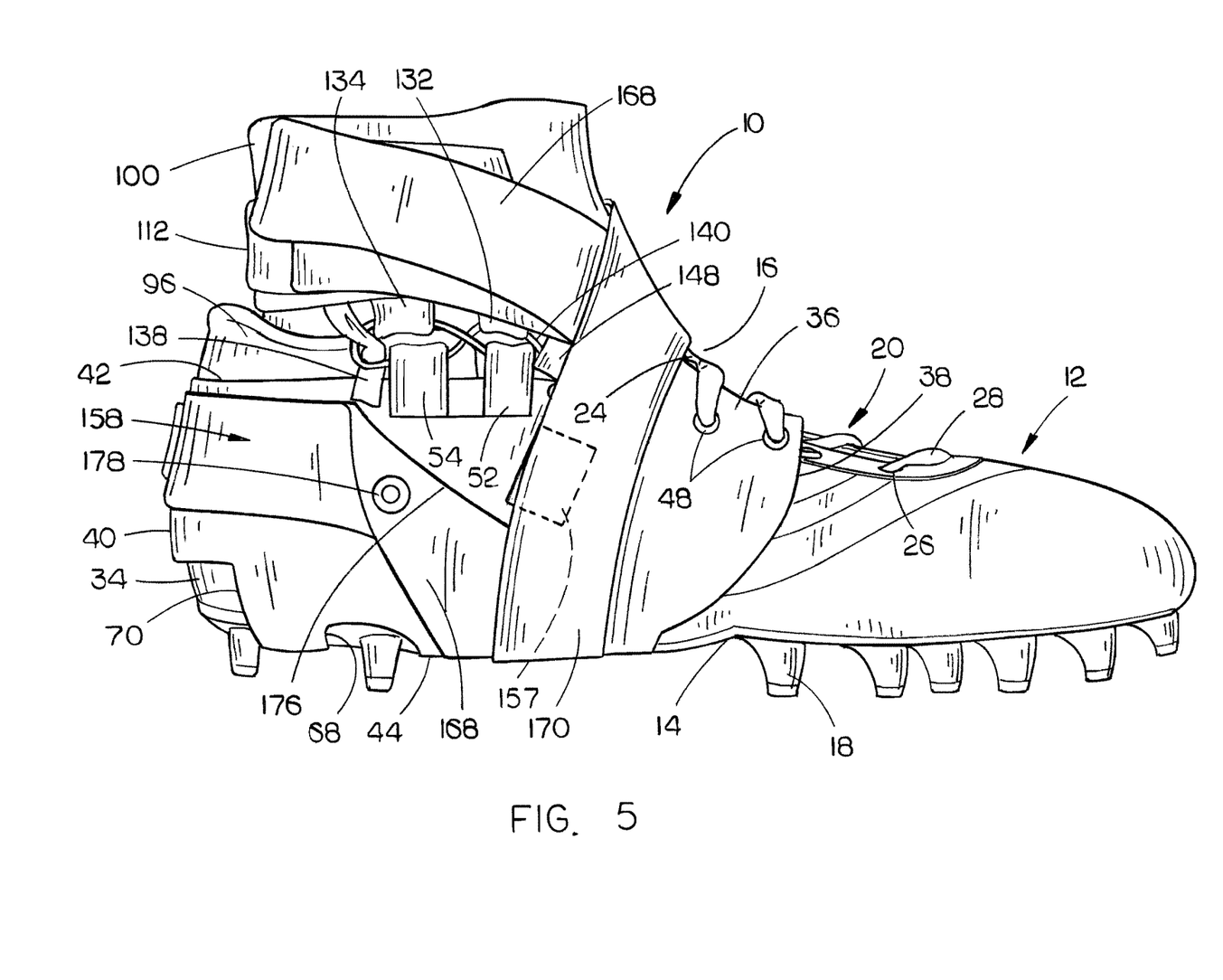
FIG. 5 is a lateral side view of the ankle brace of this invention mounted on a shoe.

As seen in FIG. 5, the ankle strap portion 168 is folded over at 176 and is maintained in the folded position by a grommet 178. Ankle strap portion 168 extends beneath the sole 14 of shoe 12, thence upwardly adjacent medial portion 56, thence towards the lateral side of the shoe, thence upwardly and rearwardly to strap 112 at the lateral side thereof. The hook fasteners 172 on the ankle strap portion 168 are then adjustably secured to the loop fasteners on strap 112 at the lateral side thereof as seen in FIG. 5.

As seen in FIG. 2, the ankle strap portion 170 is folded over at 180 and maintained in the folded position by a grommet 182. Ankle strap portion 170 extends beneath the sole 14, thence upwardly over the shoe 12 and towards the medial side of the shoe, thence adjacent the lateral side of the shoe, thence upwardly and rearwardly towards the medial side of strap 112. The hook fasteners on the free end 160 of ankle strap 112 are then adjustably secured to the loop fasteners on strap 148 and strap 112. The ankle strap 158 could be used on an ankle brace which does not have the lateral and medial tensioning cords and does not have the straps 148 and 154.

In use, the brace 10 is positioned on the shoe as generally shown in FIGS. 3-6. At this time, the lace connecting the eyelets on strap 112 is not tied, and the straps 148 and 154 are not connected to strap 112. The shoe lace 28 is threaded through some of the lower lace openings or eyelets 26 and through at least some of the eyelets 48 of lateral portion 36 and through some of the eyelets 74 of medial portion 56. The shoe lace 28 is then threaded through the remaining eyelets 26 and tied at the upper end of the shoe 12.

A lace member is then threaded through the eyelets 118, 120 at end 114 of strap 112 and through the eyelets 122 and 124 at end 116 of strap 112. The lace member is then tightened and tied. The strap 110 is then secured to the strap 100 at end 104 thereof. The free end of strap 148 is then adjustably secured to strap 112 at the second end thereof. The free end of strap 154 is then adjustably secured to strap 112 at the first end thereof.

The ankle brace 10 permits the ankle of the person to move through its natural range of motion either laterally, medially, fore and aft. When the ankle moves towards the end of its normal range of motion, the tensioning cords 140 and 146 resist further motion to protect the ankle. Ankle support is also provided by the lateral and medial portions 36 and 56. Ankle support is also provided by the flexible and stretchable member 92 which enables the person's ankle to move through its normal range of motion.

If additional support is needed beyond that which is provided by the ankle brace 10, the ankle strap 158 will be utilized. The strap 88 is disconnected from the loop fasteners 84. The strap 88 is then threaded through slits 164 and 166 of ankle strap 158. The free end of strap 88 is then secured to the loop fasteners 84. Ankle strap member 168 is then extended forwardly along lateral portion 38, thence downwardly and laterally beneath the sole 14 of shoe 12 towards the medial side 32 of shoe 12, thence upwardly, thence laterally towards lateral side 30 of shoe 12, thence upwardly and rearwardly adjacent lateral portion 36 towards the first end of strap 112. The free end of ankle strap member 158 is adjustably secured to strap 154 and strap 112.

Ankle strap member 170 is then extended forwardly along medial portion 56, thence downwardly and laterally beneath the sole 14 of shoe 12 towards the lateral side 30 of shoe 12, thence upwardly, thence laterally towards medial side 32 of shoe 12, thence upwardly and rearwardly adjacent medial portion 56 towards the second end of strap 112. The free end of ankle strap member 160 is adjustably secured to strap 148 and strap 112.

Thus it can be seen that the invention accomplishes at least all of its stated objectives.

Although the invention has been described in language that is specific to certain structures and methodological steps, it is to be understood that the invention defined in the appended claims is not necessarily limited to the specific structures and/or steps described. Rather, the specific aspects and steps are described as forms of implementing the claimed invention. Since many embodiments of the invention can be practiced without departing from the spirit and scope of the invention, the invention resides in the claims hereinafter appended.

I claim:

1. An ankle brace for use with an athletic shoe having a sole with a lower cleated surface, an upper part having an upper end, a lateral side, a medial side, with each of the lateral and medial sides having a plurality of spaced-apart lacing eyelets formed therein which have a shoe lace threaded therein, comprising:
   a lateral brace portion having a forward end, a rearward end, an upper end, and a lower end;
   said lateral brace portion being positioned adjacent the lateral side of the shoe;
   a medial brace portion having a forward end, a rearward end, an upper end, and a lower end;
   said rearward ends of said lateral and medial brace portions being operatively interconnected together;
   an upper brace portion having a forward end, a rearward end, an upper end, a lower end, a lateral side and a medial side;
   said upper brace portion positioned above said upper ends of said lateral and medial brace portions;
   a lateral tensioning cord operatively interconnecting said lateral brace portion and said lateral side of said upper brace portion;
   a medial tensioning cord operatively interconnecting said medial brace portion and said medial side of said upper brace portion;
   an elongated ankle strap;
   said ankle strap being operatively selectively removably secured, intermediate its length, to said rearward ends of said lateral and medial brace portions thereby defining a first ankle strap member with a free end and a second ankle strap member with a free end;
   said first ankle strap member extending forwardly from said rearward end of said lateral brace portion, thence downwardly therefrom, thence laterally beneath the sole of the shoe, thence upwardly adjacent said medial brace portion, thence laterally towards said lateral brace portion, thence upwardly and rearwardly with said free end of said first ankle strap member being adjustably secured to said upper brace portion at said lateral side thereof;
   said second ankle strap member extending forwardly from said rearward end of said medial brace portion, thence downwardly therefrom, thence laterally beneath the sole of the shoe, thence upwardly adjacent said lateral brace portion; thence laterally towards said medial brace portion, thence upwardly and rearwardly with said free end of said second ankle strap member being adjustably secured to said upper brace portion at;
   wherein said forward ends of said lateral and medial brace portions each have spaced-apart eyelets formed therein and wherein the shoe lace is threadably received therein.

2. The ankle brace of claim 1 further including an elongated first strap, having first and second ends, which has its said first end secured to said lateral tensioning cord and which has its said second end selectively adjustably secured to said medial brace portion and further including an elongated second strap, having first and second ends, which has its said first end secured to said medial tensioning cord and which has its said second end selectively adjustably secured to said lateral brace portion.

3. The ankle brace of claim 1 wherein said upper brace portion is generally U-shaped with spaced-apart forward end portions which are adjustably secured together.

\* \* \* \* \*